(12) United States Patent
Foreman et al.

(10) Patent No.: US 6,468,224 B1
(45) Date of Patent: Oct. 22, 2002

(54) CALIBRATED AUDIOMETER SYSTEM

(75) Inventors: Jack C. Foreman, Pflugerville; Leroy D. Braun, Austin, both of TX (US)

(73) Assignee: Bernafon, Inc., Eden Prairie, MN (US)

( * ) Notice: Subject to any disclaimer, the term of this patent is extended or adjusted under 35 U.S.C. 154(b) by 0 days.

(21) Appl. No.: 09/905,347

(22) Filed: Jul. 13, 2001

Related U.S. Application Data

(60) Provisional application No. 60/284,613, filed on Apr. 17, 2001.

(51) Int. Cl.$^7$ ................................................. A61B 5/00
(52) U.S. Cl. ...................................................... 600/559
(58) Field of Search ........................... 600/559; 73/585; 381/23.1, 60

(56) References Cited

U.S. PATENT DOCUMENTS 4,556,069 A * 12/1985 Dalton et al. ............... 600/559
5,197,332 A * 3/1993 Shennib ...................... 600/559
5,697,379 A * 12/1997 Neely et al. ................. 600/559

OTHER PUBLICATIONS

Awtrey, et al., "Transmitting Data and Power over a One-Wire Bus," Reprint from Sensors, Feb. 1997 by Dallas Semiconductor.

Dallas Semiconductor Silicon Ser. No. DS2401 prospectus, pp. 1–10.

* cited by examiner

Primary Examiner—Max Hindenburg
(74) Attorney, Agent, or Firm—Kinney & Lange, P.A.

(57) ABSTRACT

There is described a calibrated audiometer system in which the earphones have electronic identification labels which the audiometer microprocessor can interrogate to assure that the earphones which were calibrated with an audiometer are connected to the same audiometer.

4 Claims, 3 Drawing Sheets

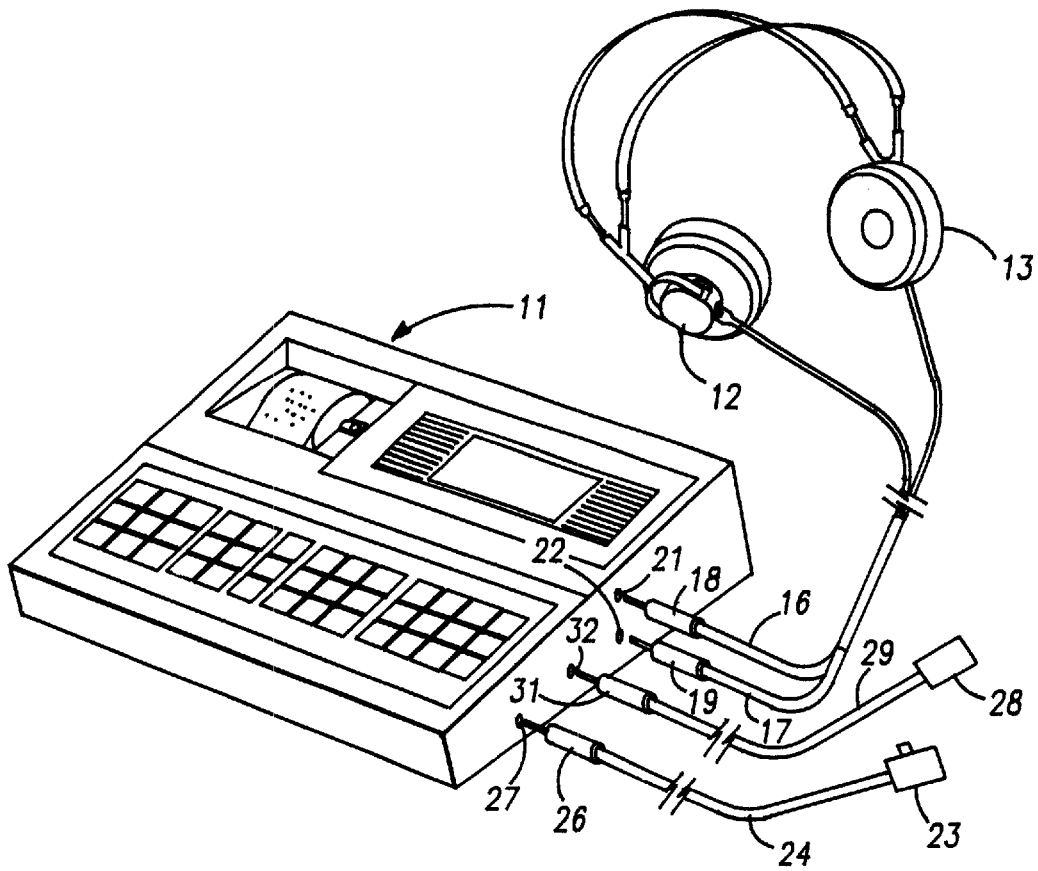
FIG.—1
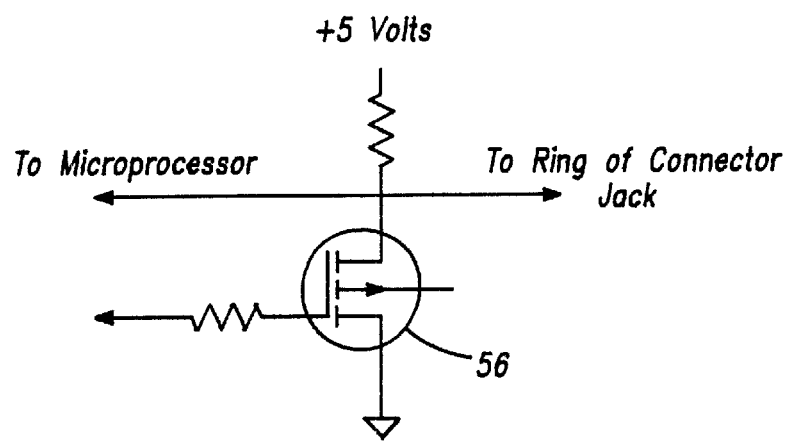
FIG.—3

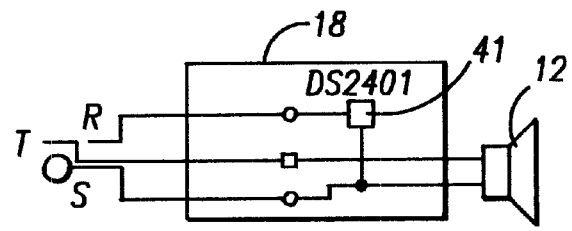
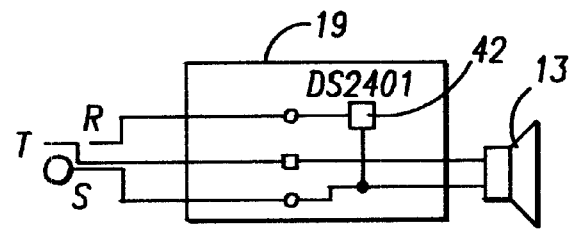
FIG.-4
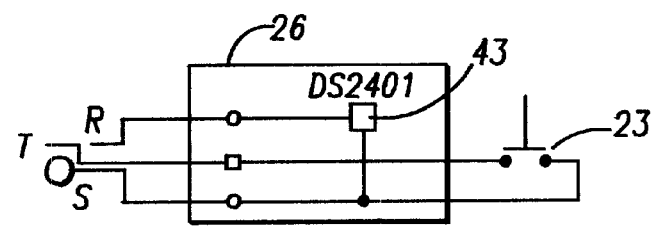
FIG.-5
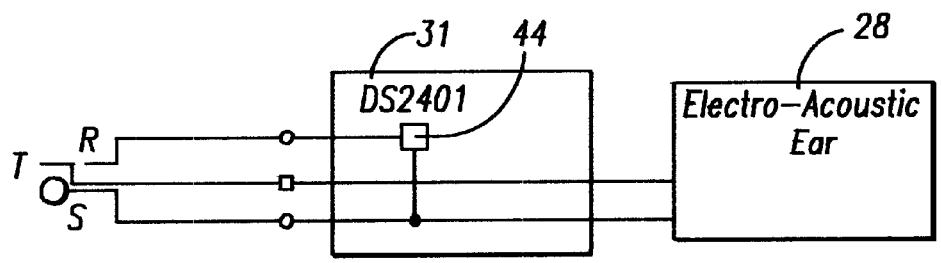
FIG.-6

CALIBRATED AUDIOMETER SYSTEM

RELATED APPLICATIONS

This application claims priority to U.S. provisional application No. 60/284,613 filed Apr. 17, 2001.

BRIEF DESCRIPTION OF THE INVENTION

This invention relates generally to a calibrated audiometer system, and more particularly to a system in which the earphones have an electronic identifying label, and to an audiometer configured to read the electronic identifying label to assure that a calibrated earphone is connected to the audiometer with which it was calibrated.

BACKGROUND OF THE INVENTION

Audiometers are used for testing hearing acuity levels of individuals. For testing, precise tones or other stimulus are presented to the subject by acoustic transducers or earphones. If the subject detects the tones or other stimulus he so indicates by depressing a patient switch. The earphones are either connected directly to the audiometer by use of industry standard stereo jacks or through the wall of a sound room by such stereo jacks connected to the audiometer. An electroacoustic ear is often used to verify calibration and monitor the ambient noise level in the sound room where the testing is conducted. A stereo plug which is inserted into a receptacle is associated with each earphone. The problem which arises is that the earphones can be connected to an audiometer with which they have not been calibrated, or in a two-wire system even with an audiometer with which they have been calibrated, they can be switched or interchanged. As a result, extreme care is required to assure that an earphone calibrated with the particular audiometer is plugged into that audiometer and that the left and right earphones are each connected to the proper jack. There is therefore a need for an audiometer system in which the audiometer can interrogate a connected earphone to assure that the proper earphone is connected to the corresponding audiometer stereo jack.

SUMMARY OF THE INVENTION

The present invention provides a calibrated audiometer system in which the earphones have electronic labels which are read by the audiometer and recorded when the earphone-audiometer combination is calibrated and later read by the audiometer and compared to the recorded label to assure that the earphones with which it was calibrated are connected to the audiometer. The invention also includes an electronic labeled patient switch and an electronic labeled electroacoustic ear which are read by the audiometer.

BRIEF DESCRIPTION OF THE DRAWINGS

The novel features that are considered characteristic of the invention are set forth with particularity in the appended claims. The invention itself, however, both as to its structure and its operation, together with additional objects and advantages thereof, will be best understood from the following description of the preferred embodiment of the invention when read in conjunction with the accompanying drawings wherein:

FIG. 1 is a schematic view of an audiometer and connected earphones, patient switch and electroacoustic ear.

FIG. 3 is a diagram of the electronic identification label interrogation circuitry.

FIG. 4 is a schematic drawing showing the left and right earphone assemblies and electronic identification labels.

FIG. 5 is a schematic drawing showing the patient switch and electronic identification label.

FIG. 6 is a schematic drawing showing the electroacoustic ear and electronic identification label.

DESCRIPTION OF PREFERRED EMBODIMENT

Figure 2:
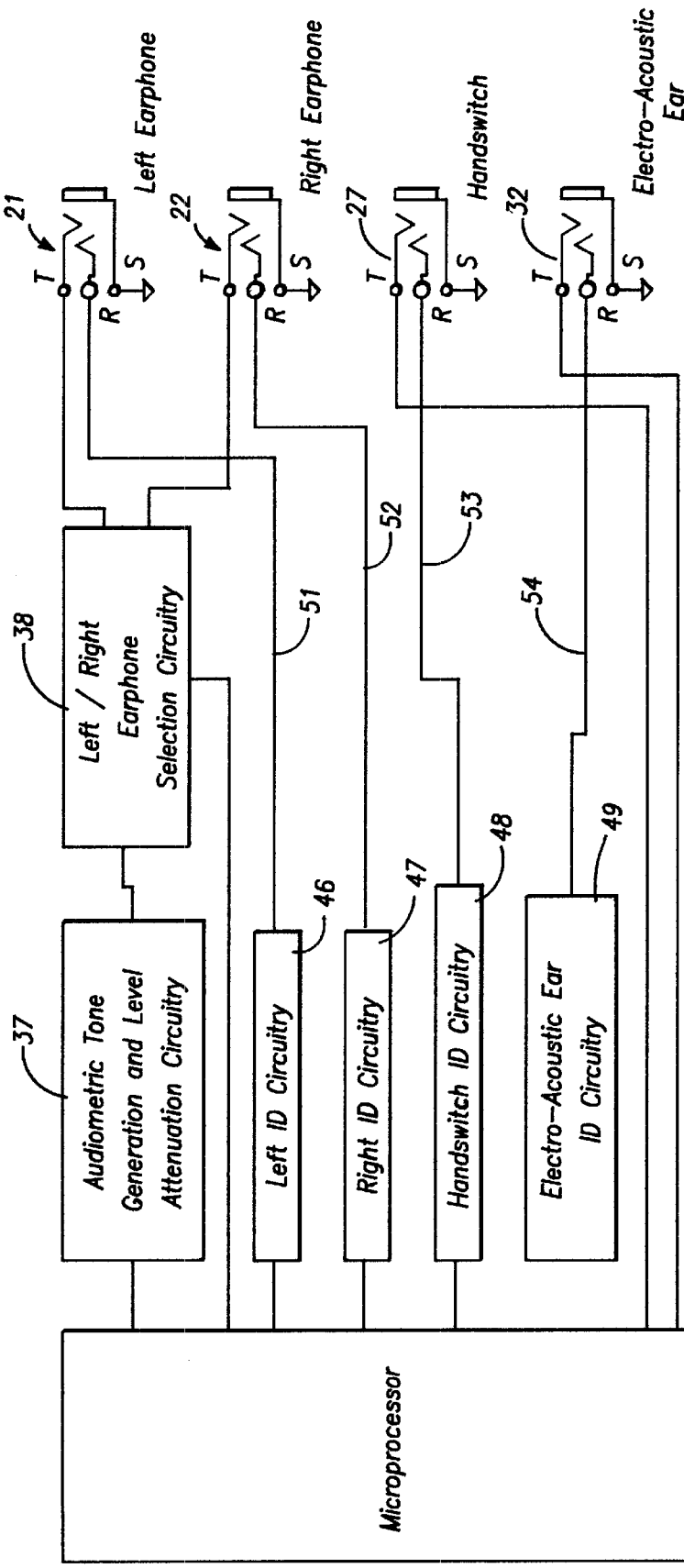
FIG. 2 is a block diagram of the audiometer microprocessor and associated circuitry for generating tone, verifying calibration, monitoring ambient noise level in the sound room, receiving patient responses and identifying the earphones, patient response switch and electroacoustic noise monitoring ear.

FIG. 1 shows an audiometer 11 connected to earphones 12 and 13 by cables 16 and 17 with plugs 18 and 19 adapted to be plugged into the corresponding receptacle 21 and 22. A patient response switch 23 is connected to the audiometer by cable 24, and connected by plug 26 received by receptacle 27. Electroacoustic ear 28 is connected to the audiometer by cable 29, plug 31 and receptacle 32. The connections of the cables to the audiometer are by industry-standard jacks 21, 22, 27, 32 which include a receptacle which receives the plug of the associated device. Generally, the audiometer is operated to provide automatic pure-tone hearing threshold testing in accordance with accepted audiometer procedures. The audiometer operation is controlled by a microprocessor 36, FIG. 2. In accordance with one embodiment of the present invention, earphones 12 and 13, FIG. 4, patient switch 23, FIG. 5, and electroacoustic ears 28, FIG. 6, are uniquely labeled by molding an electronic identification label in the plugs 18, 19, 26 and 31, respectively, and the audiometer microprocessor 36 is configured to read the labels and identify the connected device.

Turning now to FIG. 2, the microprocessor 36 controls the audiometric tone generation and level attenuation circuitry 37 which selectively provides the testing tones to the left and right earphones 12 and 13. The microprocessor controls whether the tones are applied to the left or right earphone by controlling the earphone selection circuitry 38. The tones are applied to the tip lead connection T of the associated stereo jack receptacle. Patient switch responses and electroacoustic ear responses are received by the microprocessor 36 via the tip lead connection T and processed in a conventional manner to provide test results.

The microprocessor also controls the right earphone and left earphone electronic identification labels or chips 41 and 42, the patient switch electronic identification label 43 and the electroacoustic ear electronic identification label 44, shown schematically in FIGS. 4, 5 and 6, respectively. The electronic identification labels are connected to the ring lead R of the stereo jack receptacle associated therewith. The identification labels in the preferred embodiment comprise integrated circuit chips embedded in the plugs associated with the earphones, patient switch and electroacoustic ear. In the preferred embodiment, the integrated circuit chips were DS2401 Silicon Serial Number Chips sold by Dallas Semiconductor, Dallas, Tex. As will be apparent from the following description, the electronic identification chip or label can be one of other models sold by Dallas instruments, or can be an integrated circuit from other manufacturers which can provide an identification number or label responsive to interrogation. The advantage of the DS2401 is that it can communicate over a single wire connected to the ring R of the stereo jack. The electronic identification label interrogation circuitry 46, 47, 48 and 49 for reading or interrogating the DS2401 chips or labels 41 and 42 in the earphone plugs, 43 in the patient switch plug and 44 in the electroacoustic ear plug, is identical and shown in FIG. 3.

Signals are transmitted and received serially along the lines 51, 52, 53 and 54. The differentiation between logic "0" and logic "1" is determined by the length of serial pulses which is determined by switch transistor 56 controlled by microprocessor 36. Timing is synchronized from the leading edge (high to low voltage transition) of the pulses generated by the processor. A gate voltage generated by the processor 36 triggers the transistor 56 to connect the line R to ground (low voltage) which is normally at about +5 volts (high voltage). The label chip associated with the circuit returns its identification number to the microprocessor along the corresponding line 51, 52, 53 and 54.

When the earphones 12, 13 are connected to the audiometer, the audiometer reads the chip serial number to assure that the earphone which was calibrated to the audiometer is connected. A similar identification is performed with the chips in the patient switch and an electroacoustic ear 28. In an example of interrogation, to assure that the proper earphones, switch and electroacoustic ear, or other device is connected using the DS2401 chip, the processor 36 generates pulses as follows.

1. The processor triggers the transistor to transmit a reset pulse of sufficient length as not to be confused as a data synchronization pulse. The DS2401 responds with a presence pulse. The reset pulse generated by the processor is typically 480 us while the presence pulse from the DS2401 follows within 60 us to 240 us.

2. The next step in the interrogations is the transmission by the processor of an eight (8) bit "Read ROM" command. The eight (8)-bit command is 33 h (hexadecimal) or "00110011" in binary. The least significant bit is transmitted first by the processor. The logic "1" is generated by the master pulling the buss line low for approximately 15 us. The DS2401 samples the line after 15 us to find that the line has returned to high state by the 5K pull-up resistor. In a similar fashion, a "0" is transmitted by the master by keeping the line low beyond the 15 us period so that the DS2401 will detect a low after the 15 us waiting period.

3. The read data step follows the transmission of the Read ROM command. The processor initiated the read sequence by momentarily pulling the line low and then sampling after releasing the line to see if it is allowed to return to a high state by the pull-up resistor. If the line remains low for 60 to 120 us after the leading edge of the processor pulse then the DS2401 is transmitting a "0". If not, then a "1". Sixty-four (64) bits of serial data are transmitted each time. The data set is divided into three segments. The first eight (8)-bits represent a CRC (cyclic redundancy check). The next forty-eight (48) bits are unique, and the last eight (8) bits are a family code.

4. The unique forty-eight (48) bits are then compared to those of the headset calibrated with the audiometer. If they match, the proper headset is connected, or the bits from the chips 41 and 42 are recorded and, if needed, compared.

Thus, there has been provided a calibrated audiometer system which assures that the proper earphones and/or patient switch and electroacoustic ear are connected to an audiometer. The electronic identification labels respond to inquiry by the audiometer microprocessor with a unique identifier that can be verified by the audiometer against stored data to ensure that the device is indeed the one which was calibrated with the instrument.

The foregoing descriptions of specific embodiments of the present invention have been presented for purposes of illustration and description. They are not intended to be exhaustive or to limit the invention to the precise forms disclosed, and obviously, many modifications and variations are possible in light of the above teaching. The embodiments were chosen and described in order to best explain the principles of the invention and its practical application, to thereby enable others skilled in the art to best use the invention and various embodiments with various modifications as are suited to the particular use contemplated. It is intended that the scope of the invention be defined by the claims appended hereto and their equivalents.

What is claimed is:

1. An audiometer system including earphones for supplying tones or other stimulus to a patient, said earphones including a cable and plug for connection to the audiometer, an electronic identification label associated with said earphone, and an audiometer for supplying tones and stimulus signals to said earphone and for receiving patient response including a microprocessor, said microprocessor configured to interrogate said electronic identification label to assure that earphones with which the audiometer was calibrated are connected to the audiometer.

2. An audiometer system as in claim 1 in which each of said earphones includes a plugs for connection to the audiometer and an electronic identification label is carried by each of said its plugs.

3. An audiometer system as in claims 1 or 2 including a patient switch and an electroacoustic ear, each including plugs and an electronic identification label, said audiometer configured to interrogate the identification labels of said patient switch and electroacoustic ear.

4. An audiometer system including a tone or stimulus generator, a pair of earphones for providing tones to a patient's left and right ear, a patient switch for activation by the patient in response to received tones or stimuli, an electronic identification label associate with said earphones, an electronic label associated with said switch, electronic label interrogation circuitry, a microprocessor configured to control said tone or stimulus generator to selectively apply tones to said right and left earphones, configured to receive patient response signals from said switch and process the same to provide a patient's hearing acuity, said microprocessor being further configured to control said electronic label interrogation circuitry to identify said earphones and switch.

\* \* \* \* \*

UNITED STATES PATENT AND TRADEMARK OFFICE
CERTIFICATE OF CORRECTION

PATENT NO. : 6,468,224 B1
DATED : October 22, 2002
INVENTOR(S) : Leroy D. Braun et al.

It is certified that error appears in the above-identified patent and that said Letters Patent is hereby corrected as shown below:

<u>Column 3,</u>
Line 33, delete "33 h", insert -- 33h --
Line 37, delete "buss", insert -- bus --

<u>Column 4,</u>
Line 33, delete "plugs", insert -- plug --
Line 47, delete "associate", insert -- associated --

Signed and Sealed this

Twelfth Day of August, 2003

JAMES E. ROGAN
*Director of the United States Patent and Trademark Office*